(12) United States Patent
Sampson et al.

(10) Patent No.: US 7,261,698 B2
(45) Date of Patent: Aug. 28, 2007

(54) TRANSFER NEEDLE SAFETY APPARATUS

(75) Inventors: Eric Sampson, Deltona, FL (US); Christopher S. Ronsick, Durham, NC (US)

(73) Assignee: Sherwood Services AG, Schaffhausen (CH)

( * ) Notice: Subject to any disclaimer, the term of this patent is extended or adjusted under 35 U.S.C. 154(b) by 414 days.

(21) Appl. No.: 10/422,085

(22) Filed: Apr. 24, 2003

(65) Prior Publication Data

US 2004/0215106 A1 Oct. 28, 2004

(51) Int. Cl.
*A61M 5/00* (2006.01)

(52) U.S. Cl. .................................. 600/576; 604/905

(58) Field of Classification Search .............. 604/187, 604/905, 171, 201, 202; 600/575–580
See application file for complete search history.

(56) References Cited

U.S. PATENT DOCUMENTS

| 4,150,666 A | 4/1979 | Brush ..................... 128/2 F |
| 4,320,769 A | 3/1982 | Eichhorn et al. ........... 128/763 |
| 4,808,381 A | 2/1989 | McGregor et al. .......... 422/100 |
| 4,915,702 A * | 4/1990 | Haber ....................... 604/198 |
| RE33,585 E | 5/1991 | Haber et al. ................ 604/198 |
| 5,267,983 A | 12/1993 | Oilschlager et al. ........ 604/238 |
| 5,344,417 A | 9/1994 | Wadsworth, Jr. ............ 604/414 |
| 5,358,501 A | 10/1994 | Meyer ....................... 604/414 |
| 5,360,423 A | 11/1994 | McCormick ................ 604/403 |
| 5,374,264 A | 12/1994 | Wadsworth, Jr. ............ 604/414 |
| 5,487,737 A | 1/1996 | Meyer ....................... 604/403 |
| 5,776,124 A | 7/1998 | Wald ......................... 604/403 |
| 5,893,397 A | 4/1999 | Peterson et al. ............. 141/27 |
| 6,837,872 B2 * | 1/2005 | Crawford ................... 604/110 |

* cited by examiner

*Primary Examiner*—Catherine S. Williams

(57) ABSTRACT

A transfer needle safety apparatus including a guide port adapted to fit a variety of body fluid receptacle sizes. A sleeve substantially fills the cavity inside a needle shield. The sleeve includes a robust external lead-in structure for aligning/assembling and centering the sleeve in the shield and a robust internal lead-in structure for aligning and centering a narrow body receptacle onto a needle. The sleeve engages a long section of the outer surface of a receptacle thereby preventing rocking or lateral motion of a receptacle septum relative to a needle tip. Streamlined gripping features allow removal of the sleeve from the shield.

20 Claims, 11 Drawing Sheets

TRANSFER NEEDLE SAFETY APPARATUS

BACKGROUND

1. Technical Field

The present disclosure relates to the field of medical fluid transfer devices, and more particularly, to methods and apparatus for safely transferring bodily fluids to a receptacle.

2. Description of the Related Art

In the medical field, specimens of blood or other bodily fluids are commonly obtained from a subject using a syringe and hypodermic needle or a hypodermic needle connected to a fluid collection system. Health care workers who handle fluid samples and collection apparatus are routinely exposed to dangers from inadvertent contact with contaminated needles or exposure to contaminated bodily fluids. Rigorous safety precautions must be exercised to prevent exposure to fluid samples or contaminated needles.

It is often desirable to transfer blood or other bodily fluids collected from a patient to one or more receptacles, for example, to be stored or taken to a lab for testing. Various sized receptacles such as specimen culture bottles and vials are commonly used to receive bodily fluid specimens. It is well known to cover the entry portion of a receptacle with a pierceable rubber septum which seals the entry portion and to facilitate fluid transfer to and from the receptacle. The septum is pierced by the needle or cannula of a fluid transfer device such as a medical syringe containing the fluid to be transferred. Fluid can then be safely transferred from the fluid transfer device to the receptacle. When the needle or cannula is withdrawn from the pierceable septum, the septum substantially reseals itself thereby preventing fluid from escaping the receptacle and preventing contaminants from entering the receptacle.

Fluid transfer devices such as blood collection devices are commonly adapted for transferring samples to more than one receptacle. At least one type of multiple sample adapter for a fluid transfer device provides a needle covered by a pierceable rubber sheath. Like the pierceable septum, the pierceable sheath is capable of resealing itself after a needle is withdrawn. Upon use, the needle of a multiple sample adapter pierces the rubber sheath and the septum of a receptacle. The septum allows the needle to pass into a receptacle but blocks entry of the sheath. The sheath is thus compacted along the needle shaft as the needle advances further through the sheath and the septum. As the needle is withdrawn from the receptacle, the sheath resiliently springs back along the needle shaft. When the needle tip clears the septum, the sheath takes its original shape thereby covering and sealing the needle.

A serious risk is encountered by health care workers when a needle is uncovered. The rubber sheath of a multiple collection device does not protect health care workers from accidental needle stick injuries. An accidental needle stick can be caused, for example, by slipping or improperly aiming a needle while attempting to puncture the septum of a receptacle.

Various methods and apparatus are known for reducing the risk of inadvertent contact with contaminated needles while transferring blood to a receptacle. U.S. Pat. No. 5,360,423 to McCormick (hereinafter "McCormick '423) describes a safety system for transfer and collection of body fluids. McCormick '423 describes a cup shaped guide port adaptable over a fluid transfer needle wherein the needle is recessed rearward from an open end of the guide port. An open end of the cup shaped guide port guides a fluid receiver into contact with the needle to reduce the likelihood of a needle-stick injury to a health care worker. A plurality of sized guide ports are described to guide a transfer needle into contact with a variety of fluid receivers.

McCormick '423 also describes a cap adaptable to the open end of the guide port. The cap substantially covers the open end of the guide port to reduce exposure risk to health care workers. The cap also includes a centered aperture for guiding a smaller receptacle such as a vial into contact with the needle.

Guide ports and other heretofore known safety apparatus for fluid transfer needles suffer from various drawbacks. For example, the cap described in McCormick '423 must be manually aligned and pushed onto the open end of the guide port. The finger of a health care can accidentally slip inside the guide as the health care worker attempts to install the cap onto the guide. Therefore, although the guide cap of McCormick '423 is intended to protect the health care worker, it requires an installation step that can endanger the health care worker.

The guide port described in McCormick '423 also does not provide a lead-in structure to guide a vial through the opening in the cap and into the guide port. Rather, the cap described in McCormick '423 includes a flange or outwardly directed edge around the smaller opening. The flange or outwardly directed edge can impede the installation of a vial through the opening.

The cap described in McCormick '423 contacts a vial only around a narrow circumference at a proximal position on the vial. Therefore, the center axis of the vial is not robustly aligned and located relative to the center axis of a needle. The vial's freedom of movement can allow lateral movement of the vial's septum relative to the needle tip. Lateral movement of the septum relative to the needle can tear the septum which can prevent the septum from resealing properly after use. Such tears can allow dangerous fluids to escape from the receptacle or allow contamination into a receptacle. Lateral movement of a vial or receptacle relative to the needle can similarly tear a needle sheath and allow dangerous fluid to escape from a fluid transfer device.

Various guide ports heretofore known must be provided in a plurality of sizes to accommodate a variety of receptacle sizes. Heretofore known guide ports are also typically designed for use with a single fluid transfer device. The single fluid transfer device typically includes a needle permanently mounted inside of the guide port and permanently attached to tubing or a syringe mounted outside of the guide port. The needle is connected to the tubing or syringe via at a neck portion of the guide port.

Therefore, it would be desirable to overcome the disadvantages and drawbacks of the prior art with a guide port including a sleeve that substantially fills the cavity inside the guide port preventing a user who is holding the sleeve on the outside rim from having his finger slip between the sleeve and the needle. It would be desirable if such a guide included a sleeve having a robust external lead-in structure for aligning/assembling and centering the sleeve in the guide and a robust internal lead-in structure for aligning and centering a vial onto a needle. It would be desirable to provide a guide that engages long section of the outer surface of a vial thereby preventing rocking of a receptacle or lateral motion of the septum relative to the needle tip. It would also be desirable to provide a guide adapted to fit a variety of sized receptacles. It would also be desirable to guide port adapted for use with multiple fluid transfer devices.

SUMMARY

Accordingly, a transfer needle safety apparatus is provided that is adapted to fit a variety of fluid receptacles. The transfer needle safety apparatus includes a shield for use with wide body receptacles and a removable sleeve which adapts the shield for use with narrow body receptacles. The sleeve includes a robust external lead-in structure for aligning and centering the sleeve in a shield and a robust internal lead-in structure for aligning and centering a vial onto a needle. The sleeve engages an extended area along the outer surface of a vial thereby aligning the vial and preventing rocking or lateral motion of the vial's septum relative to a needle tip. The sleeve substantially fills the cavity of a shield thereby preventing a user's finger from slipping between the sleeve and the shield.

Internal stepped shoulders are provided in the shield to guide and center a variety of sized receptacles. A tubular extension protruding distally from the shield includes features for attachment and removal of multiple fluid transfer devices to and from a single shield. Snap features provide audible and/or tactile indications of full insertion of a sleeve to a shield. Gripping features are provided for removal of the sleeve from the shield. Streamlined gripping features prevent accidental disengagement of the sleeve from the shield.

In one particular embodiment, a needle shield for safe transfer of body fluids to a container is provided. The needle shield comprises an outer cylinder having a wide diameter side-wall defining a large substantially full diameter proximal end opening and a narrower diameter distal end wall having an open tubular extension extending distally therefrom. The outer cylinder has an inside diameter adapted to receive a wide body collection vessel. The tubular extension is adapted to retain a transfer needle and mate with a fluid transfer device. For example, the tubular extension can include threads or other mating features for removable attachment to a male luer of a fluid transfer syringe. The outer cylinder has a depth sufficient to extend beyond a transfer needle tip when a transfer needle is installed in the tubular extension.

The needle shield includes a removable sleeve comprising an inner cylinder defining a proximal open end and having an inside diameter adapted for receiving a narrow body collection vessel. A plurality of ribs extends radially from an outside surface of the inner cylinder to the inside diameter of the outer cylinder. The inside cylinder has an open distal end.

In at least one embodiment, the proximal opening of the inner cylinder has an annular flange extending from the inner cylinder to a diameter equal or greater than the large opening in the outer cylinder. In an alternative embodiment, the proximal opening includes a shoulder having at least one finger protruding radially therefrom. A slot can be provided in the outer cylinder side wall adjacent the outer cylinder's proximal end opening to accept a finger protruding radially from the sleeve when the sleeve is installed in a needle shield.

A radial protrusion such as a flange or finger extending from a sleeve may be accidentally pushed or bumped in a proximal direction thereby accidentally disengaging the sleeve from the needle shield. Accordingly, still another embodiment is provided wherein the inner cylinder's proximal opening is defined by a cylindrical proximal extension. The cylindrical proximal extension allows a user to grip the sleeve. The proximal extension thereby provides for removal of a sleeve from a needle shield without having a radial protrusion such as a flange or finger extending from the sleeve. In still another embodiment, at least one slot is provided in the outer cylinder side wall adjacent the outer cylinder's proximal end opening to allow gripping and removal of the sleeve without requiring a radial protrusion or proximal extension from the sleeve.

In an illustrative embodiment, a snap feature provides audible and/or tactile feedback to the user to indicate that a sleeve is fully installed to the needle shield. Such feedback can prevent a user from applying excessive or insufficient force when installing the sleeve to a needle shield. A snap feature such as an undercut or annular ring can be formed in the inside diameter of the needle shield to provide a snap-fit with a cooperating feature in the sleeve. For example, a step can be provided in the proximal end of at least one rib to accept an annular ring in the shield. Such snap features also provide retention of the sleeve within the needle shield. An annular ring or other snap feature that extends around the full diameter of the shield provides a 360 degree snap fit without requiring rotational orientation of the sleeve to the shield Each of the ribs includes an inclined alignment surface that engages the rim of the outer cylinder when the sleeve is installed to the removable shield. The ribs cause the sleeve to become aligned coaxially with the shield during installation thereto. Coaxial alignment of the sleeve within the shield is completed before the distal end of the inner cylinder of the sleeve reaches the needle tip. This early centering of the sleeve prevents interference between a needle tip and the removable shield which could damage the needle or a needle sheath.

In a particular embodiment, at least one of the ribs includes a rib extension extending distally from the rib's inclined alignment surface. Clearance windows are provided in the shield and disposed to allow protrusion of the rib extensions there-through when the sleeve is assembled to the shield. Protrusion of the rib extensions through the clearance windows facilitates removal of the sleeve from the needle shield by applying force in a proximal direction on the rib extensions while holding the needle shield.

In at least one embodiment, the shield includes a pre-installed needle to form a transfer needle safety apparatus. The needle is non-removably installed in the distal end opening of the needle shield and extends proximally into the cavity of the needle shield. A resilient needle sheath is optionally installed around the needle and attached to form a seal at its distal end against an inside wall of the needle shield.

In another illustrative embodiment, a method is provided for safely transferring body fluids to a vessel comprising fitting fluid transfer needle assembly to an adapter protruding from the closed distal end of a wide mouthed needle shield. Then a receptacle having a puncturable septum is fitted into the wide open end of the wide mouthed needle shield so that the septum is punctured with the needle. Next fluid is transferred from the said needle into the receptacle. The receptacle is then removed from the shield and a sleeve is installed to the shield to adapt the shield for receiving a tube. A tube having a puncturable septum can then be fitted into the sleeve so that the septum is punctured with the needle. Fluid can then be transferred safely to the tube.

BRIEF DESCRIPTION OF THE DRAWINGS

The foregoing and other features and advantages of the present invention will be more fully understood from the following detailed description of illustrative embodiments, taken in conjunction with the accompanying drawings in which.

DETAILED DESCRIPTION OF EXEMPLARY EMBODIMENTS

Figure 1:
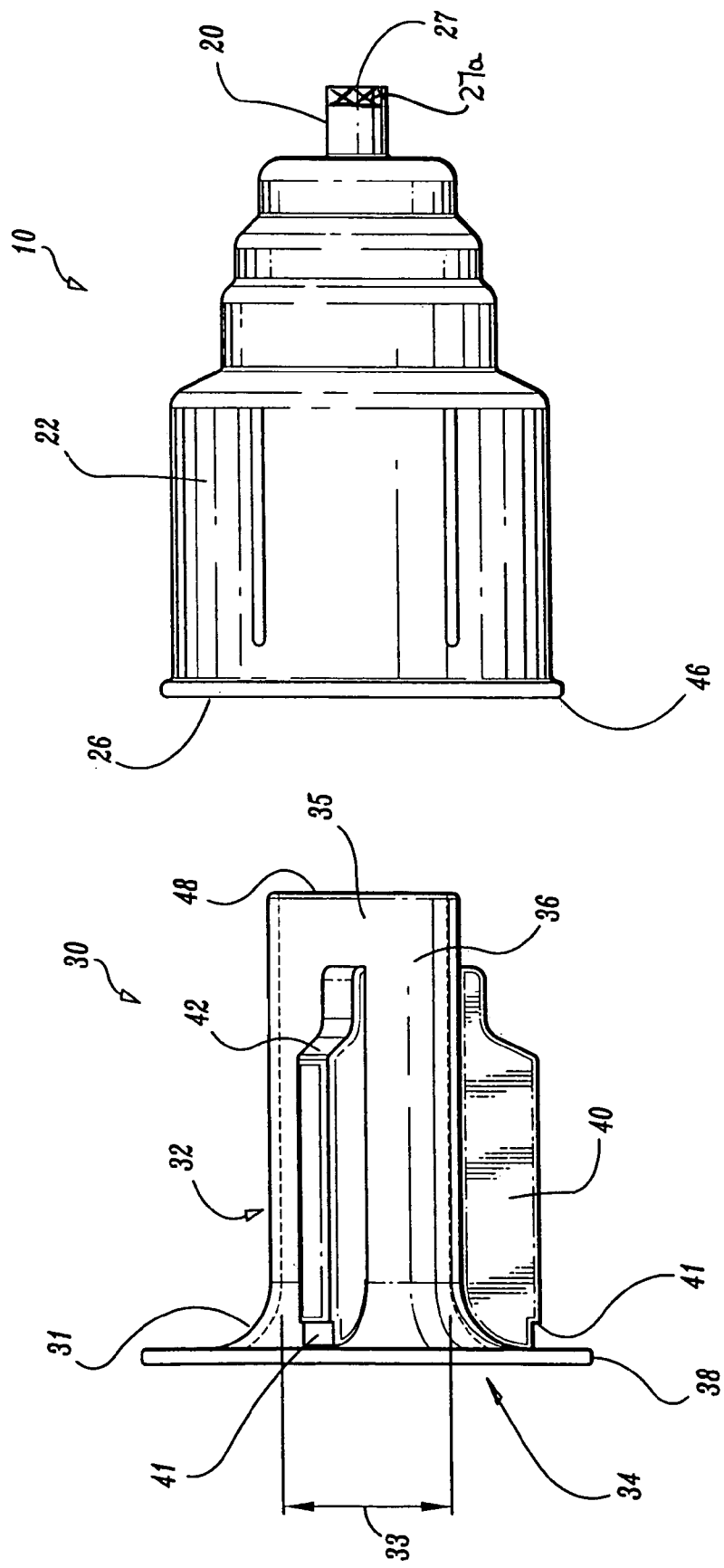
FIG. 1 is a diagrammatic representation of a removable sleeve aligned with a needle shield according to the disclosure.

The present invention will be described in detail with respect to blood collection applications with the understanding that embodiments of the present invention are directed to various other fluid transfer applications as well.

In the discussion that follows, the term "proximal" will refer to the portion of a structure that is closer to a practitioner, while the term "distal" will refer to the portion that is further from the practitioner. As used herein, the term "subject" refers to a human patient or other animal. According to the present disclosure, the term "practitioner" refers to a doctor, nurse or other care provider and may include support personnel.

Referring to FIGS. 1-4, a transfer needle safety apparatus includes a shield 10 having a wide diameter proximal end side-wall 22 defining cavity 44. The cavity 44 has a rim 46 defining a substantially full diameter proximal opening 26. The cavity 44 also has a narrower diameter distal end wall 18 with an open tubular extension 20 extending distally therefrom. The inner contour 54 of the shield 10 is adapted to receive a wide body collection vessel 50.

Figure 10:
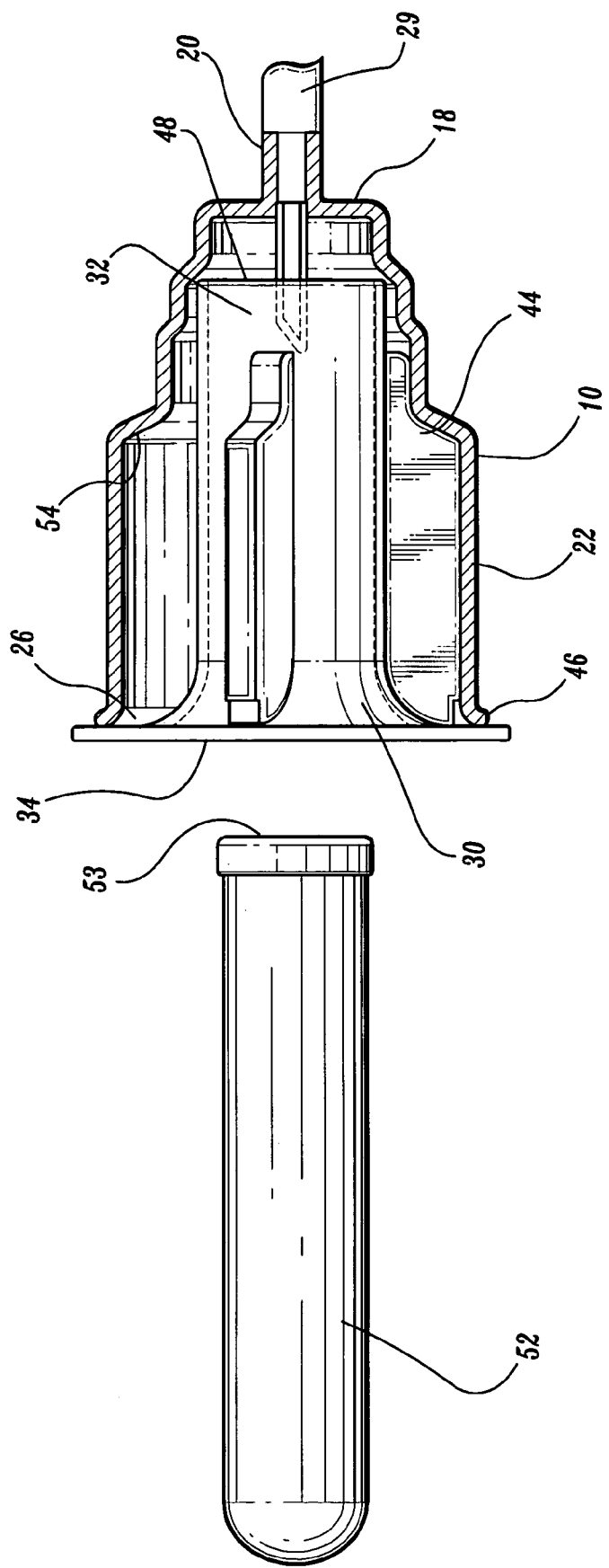
FIG. 10 is a cross sectional view of a transfer needle safety apparatus and a fully installed removable sleeve aligned with a narrow body collection vessel according to the disclosure.
Figure 11:
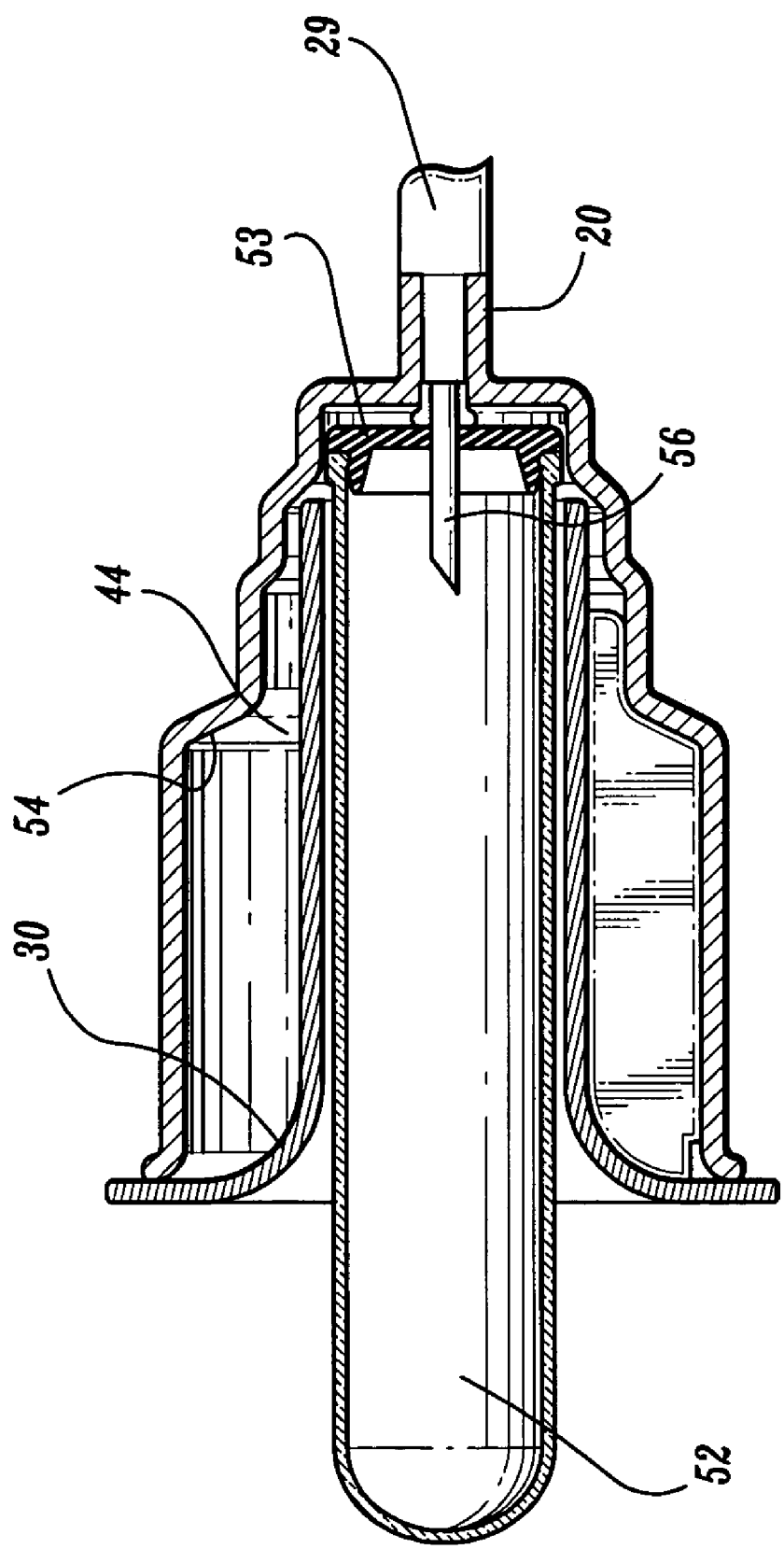
FIG. 11 is a cross sectional view of a transfer needle safety apparatus and a fully installed removable sleeve with a fully installed narrow body collection vessel according to the disclosure.

The transfer needle safety apparatus also includes a removable sleeve 30 adapted to fit into the cavity 44 of the shield 10 and self align coaxially therewith. The removable sleeve 30 has an inner cylinder 32 defining a proximal opening 34 and a distal opening 48 and an inside diameter 33 adapted for receiving a narrow body collection vessel 52 (FIGS. 10, 11). In an illustrative embodiment, the proximal opening 34 of the inner cylinder 32 includes an annular flange 38 extending radially beyond the rim 46 of proximal opening 26. In at least one illustrative embodiment the flange 38 includes a rounded shoulder 31 blending into the proximal opening 34 of the inner cylinder 32.

In an illustrative embodiment, the transfer apparatus includes a plurality of ribs 40 extending radially from the outer surface 35 of the inner cylinder 32 to a diameter corresponding to the inner contour 54 and cooperatively engages with the shield side-wall 22 to provide coaxial alignment of the sleeve 30 with the shield 10.

In at least one embodiment, the transfer apparatus includes a transfer needle 56 non-removably installed with the shield 10. The transfer needle 56 extends proximally into the cavity 44 from the distal end wall 18, and distally into the tubular extension opening 27. The sidewall 22 extends beyond the tip 57 of the transfer needle 56. Optionally, a re-sealable needle sheath 58 is non-removably installed over the transfer needle 56 and sealed against the distal end wall 18.

In an illustrative embodiment, a tubular extension 20 includes mounting structure 27a, shown schematically in FIG. 1, adapted for mounting to a luer 29 of a fluid transfer syringe. The mounting structure 27a of tubular extension 20 can include threads adapted for attachment to a threaded luer 29 of a fluid transfer syringe. Alternatively, mounting structure 27a can be positioned in opening 27 of tubular extension 20 and can include a distal end inside diameter of opening 27 adapted for receiving a male luer 29 of a fluid transfer syringe. In still another embodiment, mounting structure 27a can include a luer-lock fitting positioned on tubular extension 20 for removable attachment to a cooperating luer lock fitting (not shown) of a fluid transfer syringe.

In at least one illustrative embodiment, side wall 22 of shield 10 includes an internal undercut (not shown) adjacent to the rim 46. At least one of the ribs 40 includes an inwardly formed step 41 which engages the undercut when the sleeve 30 is installed in the needle shield 10 for removable retention of the sleeve 30 in the cavity 44. In another illustrative embodiment, the inside diameter 43 of shield 10 provides an interference fit with the ribs 40 for removable retention of the sleeve 30 in the cavity 44.

In still another embodiment, each of the ribs 40 include an inclined distal end alignment surface 42 for aligning the sleeve 30 with the shield 10 when the alignment surface 42 engages the rim 46 during installation of the sleeve 30 to the shield 10.

In at least one embodiment, each of the ribs 40 extend far enough distally to engage the side-wall 22 and ensure alignment of the sleeve 30 within the shield 10 before the distal end of the inner cylinder 32 reaches the transfer needle tip 57 during installation of the sleeve 30 to the shield 10.

Figure 2:
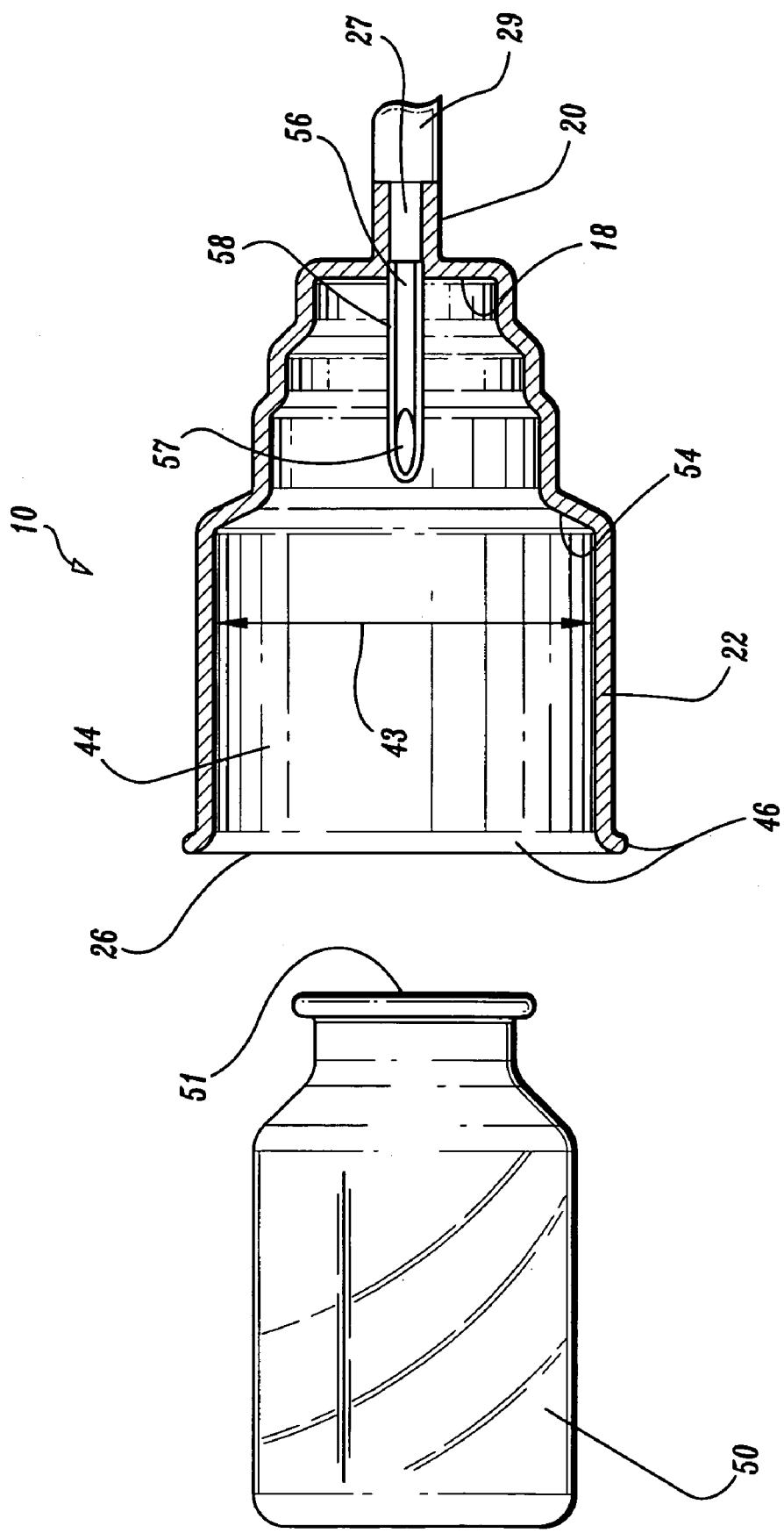
FIG. 2 is a cross sectional view of a transfer needle safety apparatus aligned with a wide body collection vessel according to the disclosure.
Figure 3:
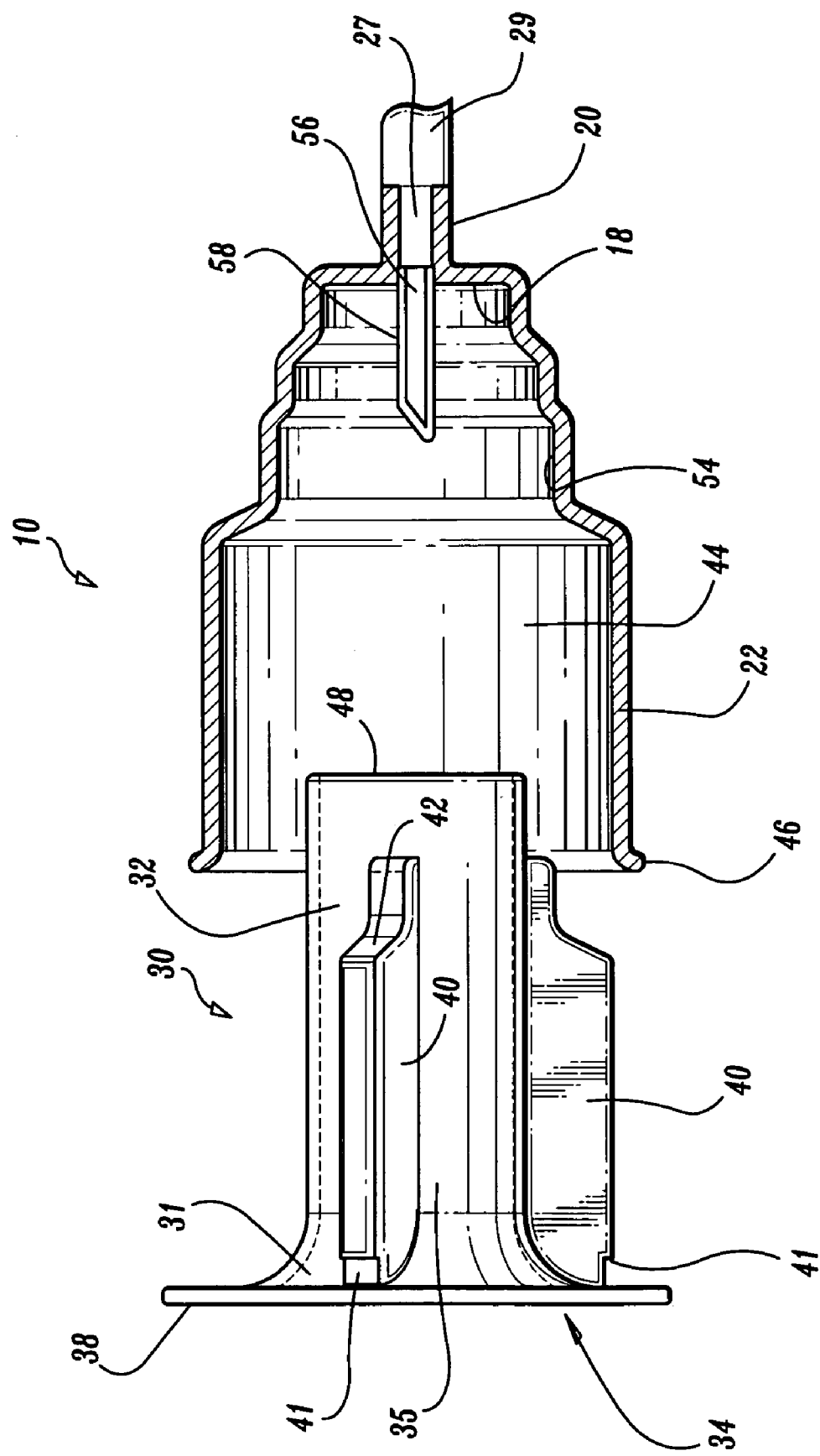
FIG. 3 is a cross sectional view of a transfer needle safety apparatus and a partially installed removable sleeve according to the disclosure.
Figure 4:
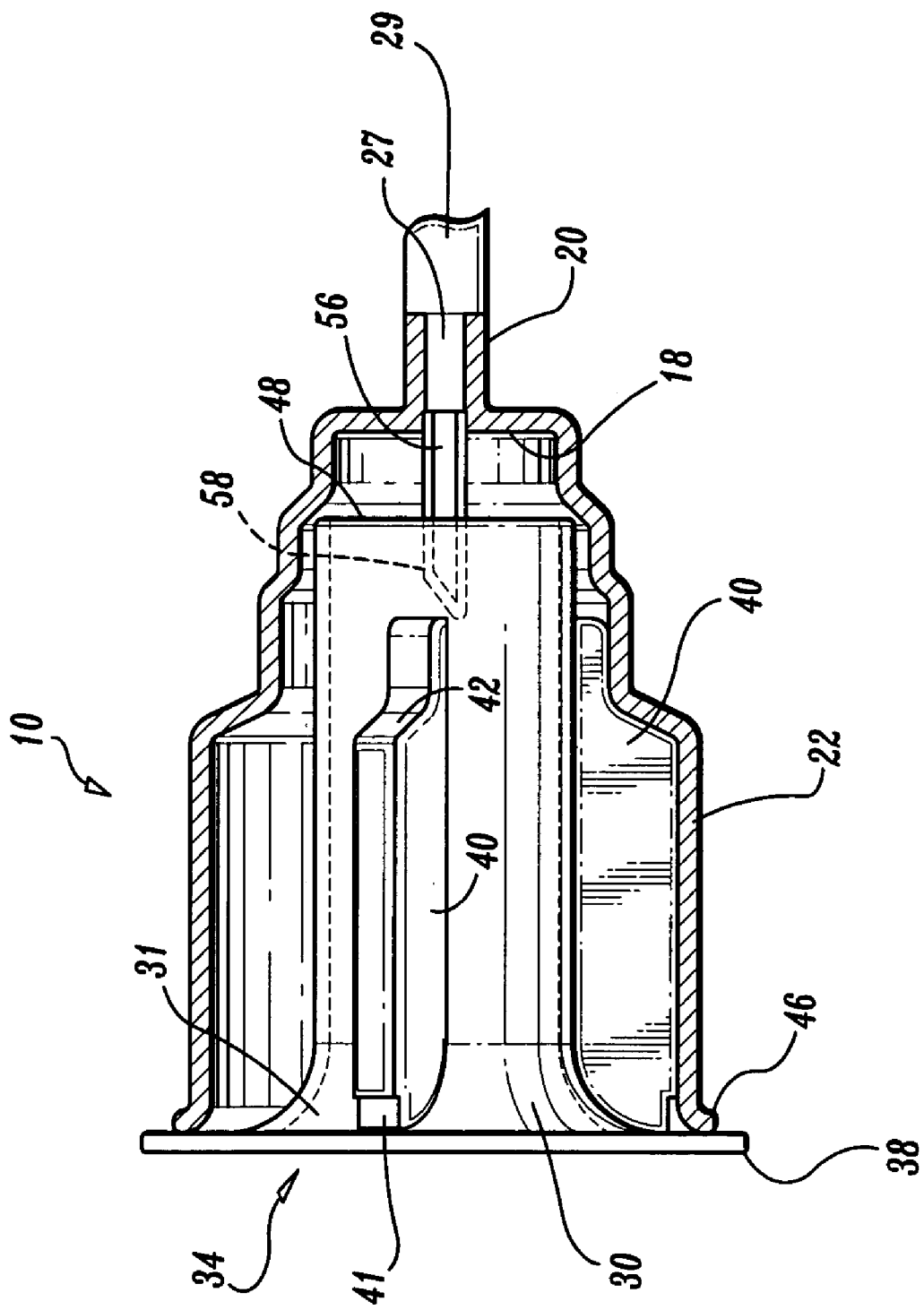
FIG. 4 is a cross sectional view of a transfer needle safety apparatus and a fully installed removable sleeve according to the disclosure.
Figure 5:
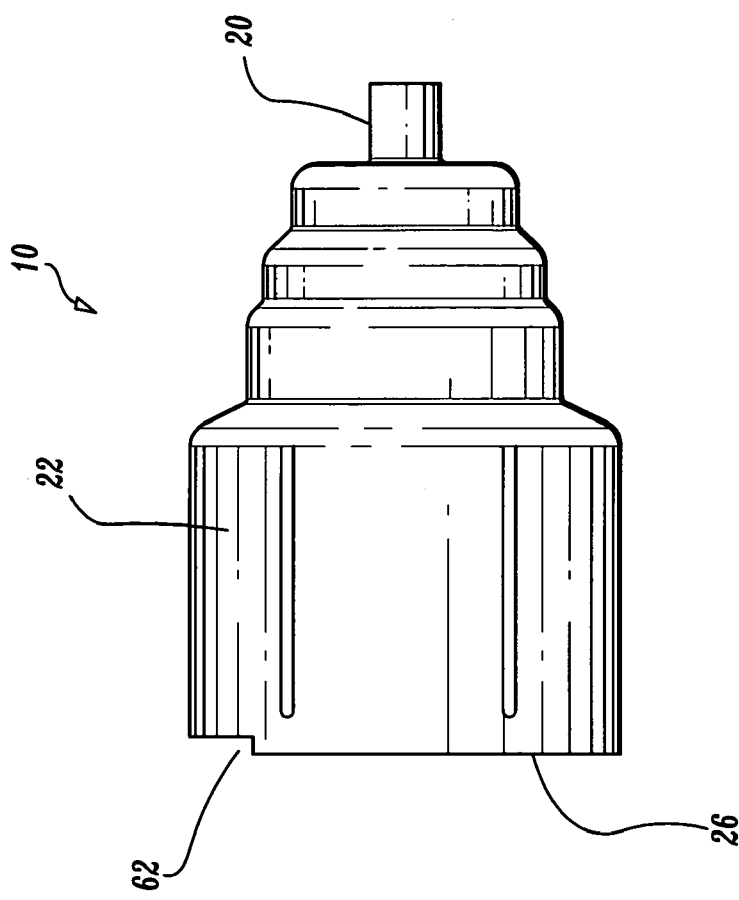
FIG. 5 is a diagrammatic representation of a removable sleeve having a radially protruding finger aligned with a shield having a slot according to an alternative embodiment.
Figure 5:
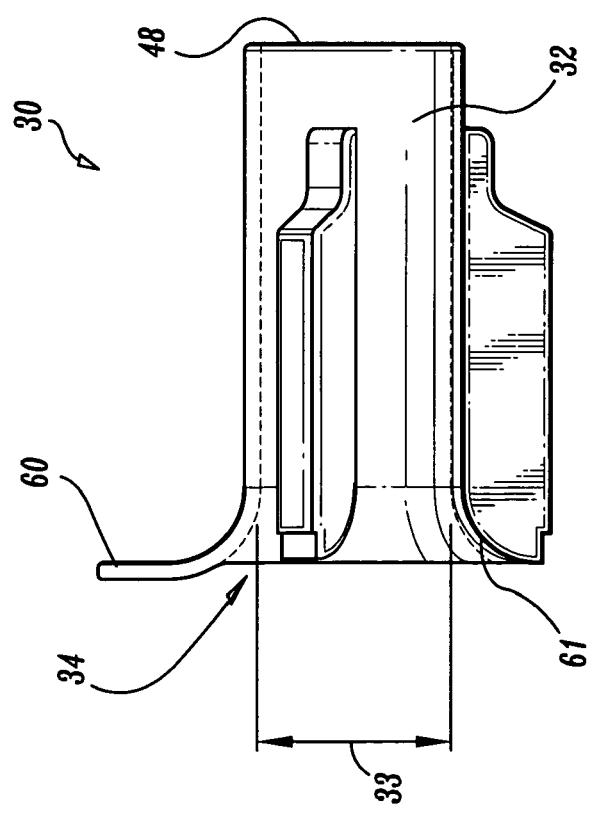
Figure 6:
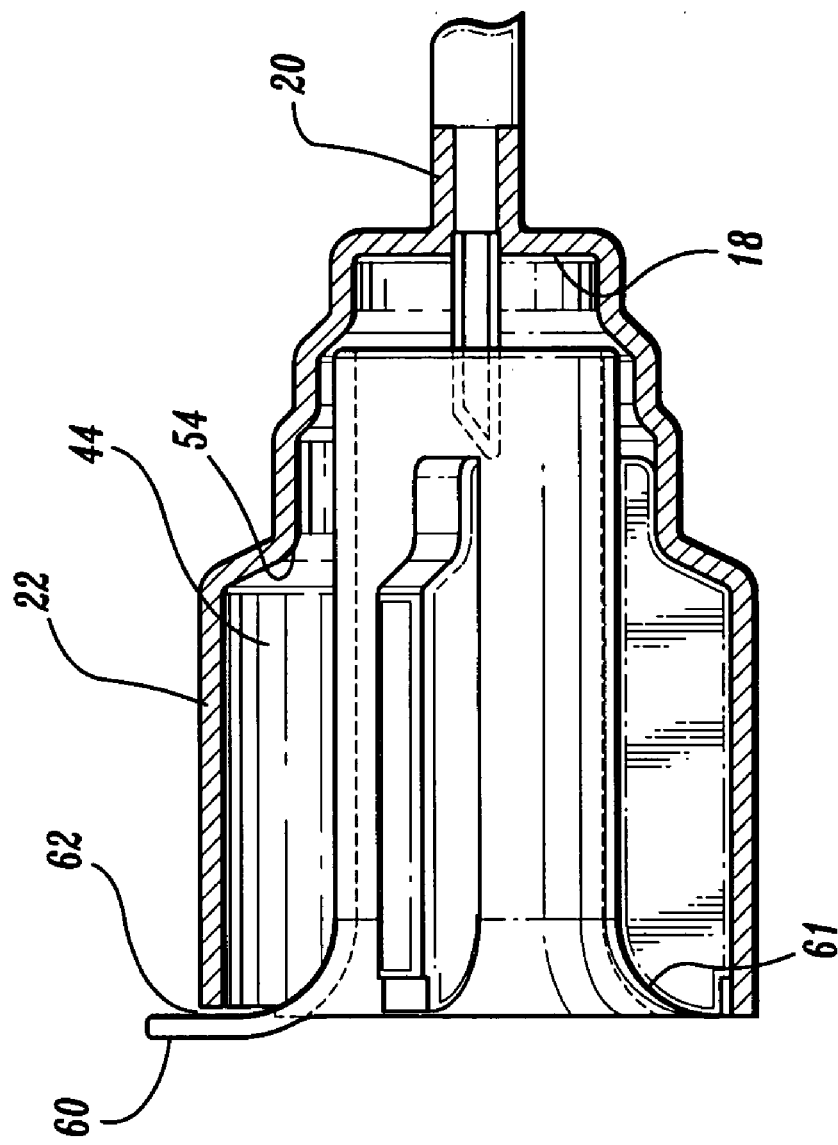
FIG. 6 is a cross sectional view of a transfer needle safety apparatus and a fully installed removable sleeve according to an alternative embodiment.

Referring now to FIGS. 5 and 6, another illustrative embodiment of a transfer needle safety apparatus is shown including a shield 10 having a side-wall 22 defining a cavity 44 with a substantially full diameter proximal opening 26 and having a narrower diameter distal end wall 18 with an open tubular extension 20 extending distally therefrom. The shield 10 includes an inner contour 54 adapted to receive a wide body collection vessel 50 (FIG. 2). A removable sleeve 30 is adapted to fit into the cavity 44 and self align coaxially therewith. The removable sleeve 30 comprises an inner cylinder 32 defining a proximal opening 34 and an distal opening 48 and having an inside diameter 33 adapted for receiving a narrow body collection vessel 52 (FIGS. 10, 11). A finger 60 extends from the proximal opening 34 of the inner cylinder 32. The finger 60 extends to a diameter equal or greater than the proximal opening 26 of the shield 10. The side-wall 22 of the shield 10 includes a slot 62 disposed therein configured to receive the finger 60 of the removable sleeve 30. In at least one embodiment, the inner cylinder 32 includes a rounded shoulder 61 flaring outwardly to a diameter corresponding to the cavity inside diameter.

Figure 7:
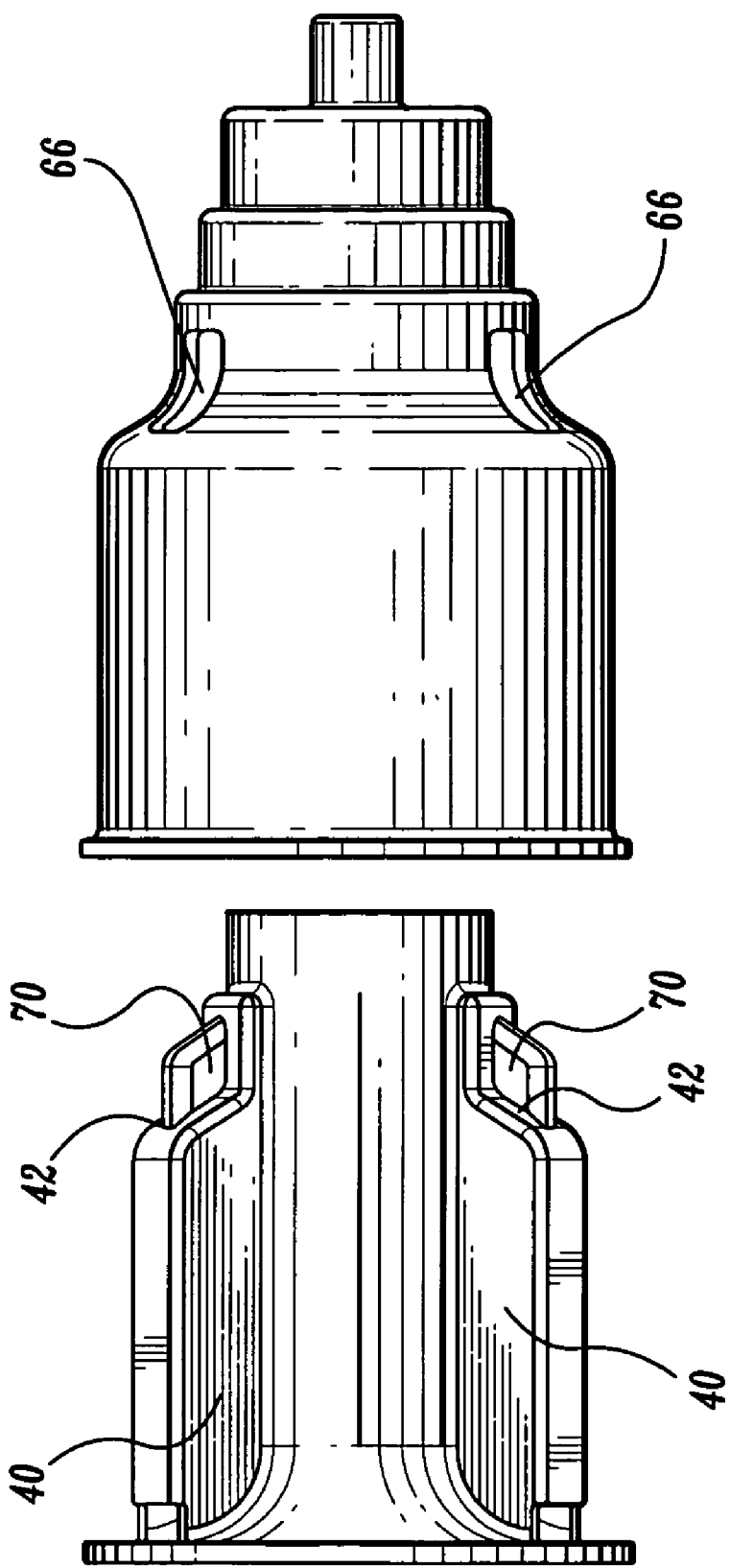
FIG. 7 is a diagrammatic representation of a removable sleeve having rib extensions aligned with a shield having clearance windows to accept the rib extensions according to an alternative embodiment.

Referring now to FIG. 7, an alternative embodiment of the sleeve 30 and shield 10 according to the disclosure includes at least one rib extension 70 protruding distally from the inclined surface 42 of at least one rib 40. At least one corresponding clearance window 66 is provided in shield 10 to accept the rib extension 70 when the sleeve 30 is installed in the shield 10. No radial protrusion from the sleeve such as a finger 60 (FIGS. 5, 6) or flange 38 (FIGS. 1-4) is required because removal of the sleeve 30 from the shield 10 can be effected by pushing on the rib extensions 70 while holding the shield 10.

Figure 8:
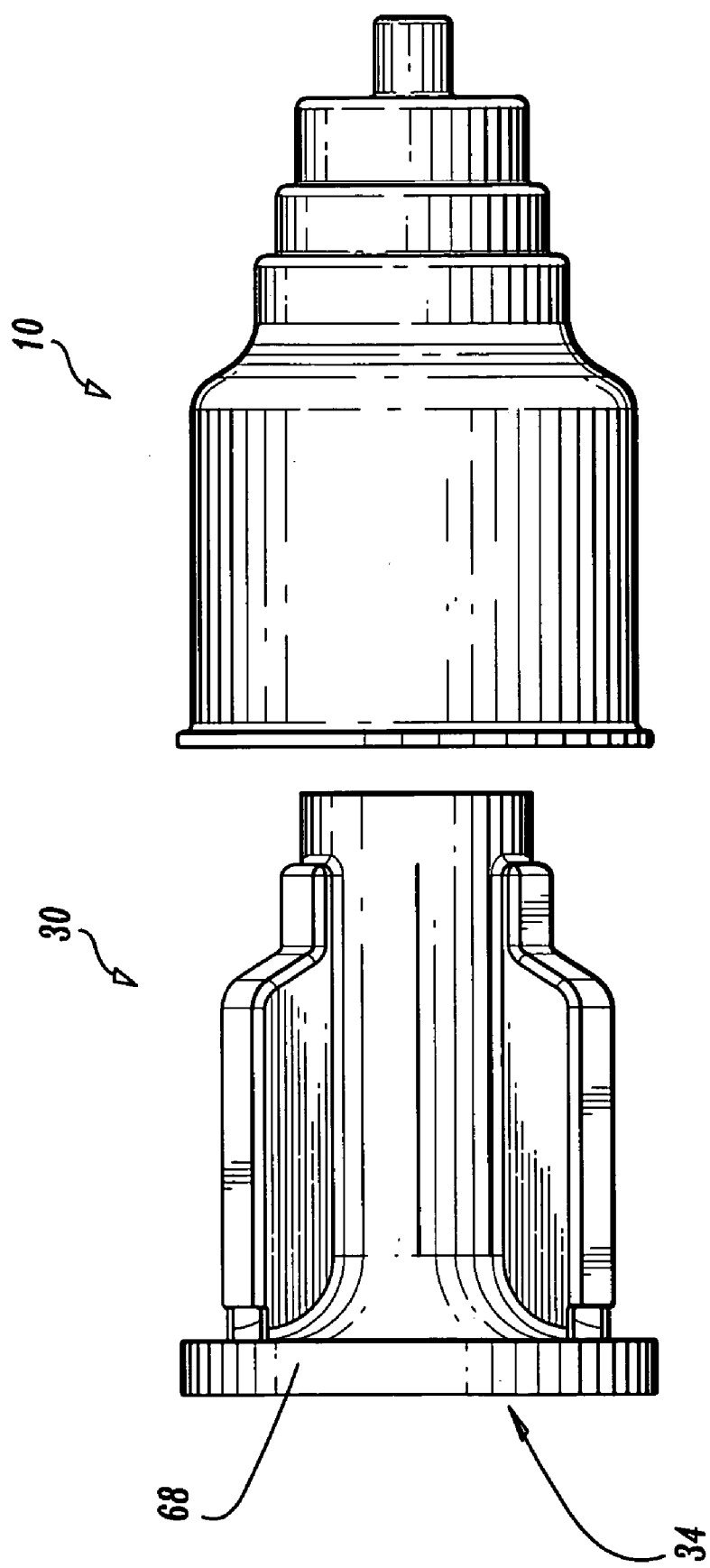
FIG. 8 is a diagrammatic representation of a removable sleeve having a cylindrical proximal extension aligned with a shield according to an alternative embodiment.

Referring to FIG. 8, an alternative embodiment of the sleeve 30 according to the disclosure includes a cylindrical proximal extension 68 surrounding the proximal opening 34 of the sleeve 30. No radial protrusion from the sleeve 30 is required because removal of the sleeve 30 from the shield 10 can be effected by gripping the proximal extension 68 to pull the sleeve 30 proximally while holding the shield 10.

Figure 9:
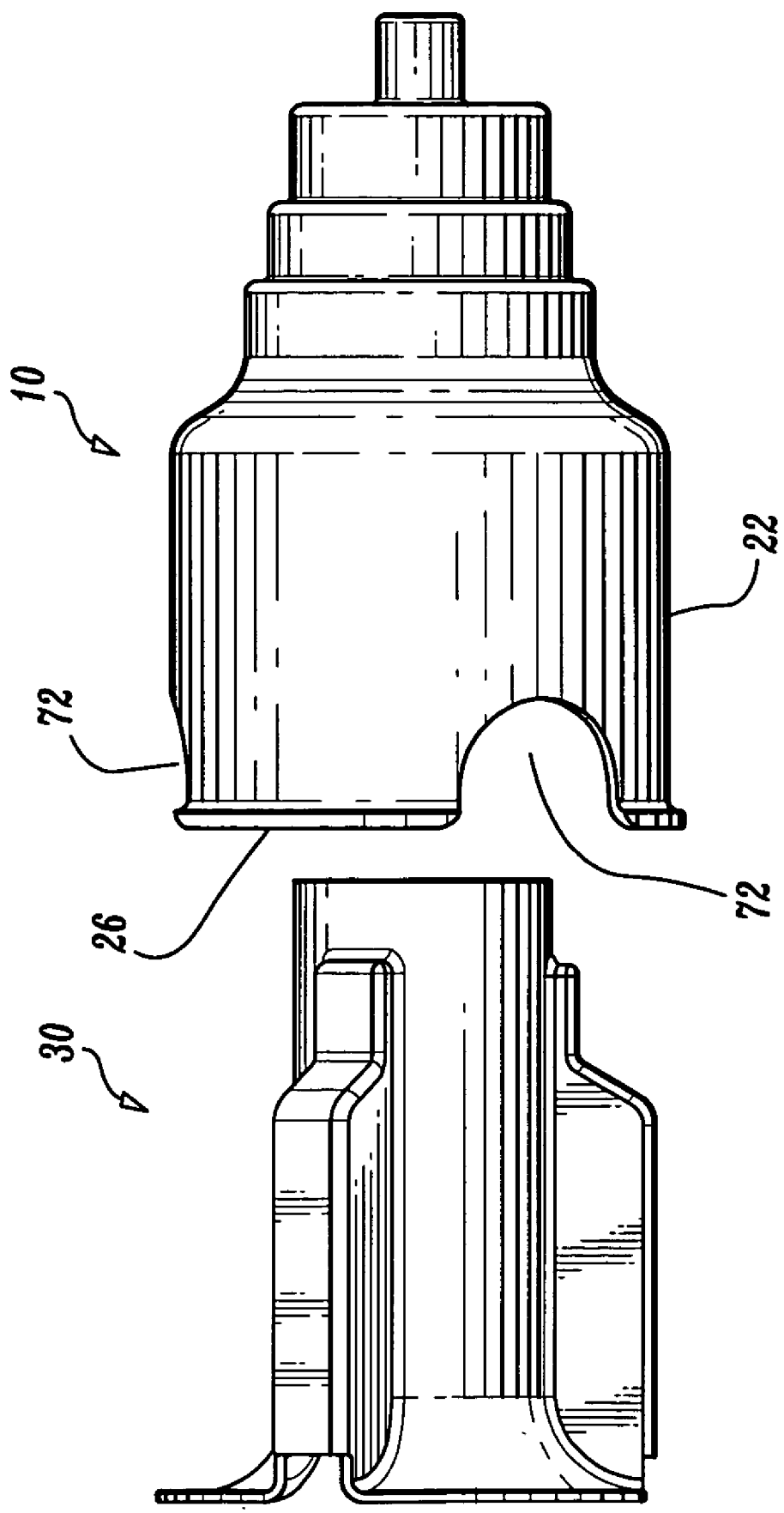
FIG. 9 is a diagrammatic representation of a removable sleeve aligned with a shield having a plurality of slots according to an alternative embodiment.

Referring to FIG. 9, an alternative embodiment of the sleeve 30 and shield 10 according to the disclosure includes at least one slot 72 in the side wall 22 of shield 10 adjacent the shield's proximal opening 26 to allow gripping and removal of the sleeve 30 without requiring a radial protrusion or proximal extension 68 (FIG. 8) from the sleeve 30.

The present disclosure also provides a method for safely transferring body fluids to a vessel. Referring now to FIGS. 10 and 11, the method includes providing a shield 10 having a side-wall 22 defining a cavity 44 with a rim 46 defining a substantially full diameter proximal opening 26. The shield 10 has a narrower diameter distal end wall 18 with an open tubular extension 20 extending distally therefrom. The shield 10 also includes an inner contour 54 adapted to receive a wide body collection vessel 50 (FIG. 2). A fluid transfer needle 56 is permanently installed with the shield 10 and extends from the proximal end of the tubular extension 20 into the cavity 44.

A removable sleeve is 30 adapted to fit into the cavity 44 and self align coaxially therewith. The removable sleeve 30 comprises an inner cylinder 32 defining a proximal opening 34 and a distal opening 48 and having an inside diameter adapted for receiving a narrow body collection vessel 52.

According to the method of an illustrative embodiment, a luer 29 of fluid transfer device such as a syringe is fitted to the distal end of the tubular extension 20. In one illustrative embodiment, the luer of a transfer syringe is fitted to the tubular extension 20 by engaging threads disposed on the luer 29 with cooperating threads disposed on the tubular extension 20. A narrow body fluid collection vessel 52 having a penetrable septum 53 is inserted into the sleeve 30 so that the septum 53 is penetrated by the transfer needle tip 57. Fluid from the fluid transfer syringe is transferred into the narrow body receptacle 52. The narrow body receptacle 52 is then removed from the sleeve 30.

In an illustrative embodiment of method according to the present disclosure, the sleeve 30 is then removed from the shield 10. Referring again to FIG. 2, a wide body fluid receptacle 50 having a penetrable septum 51 is inserted into the shield 10 and so that the septum 51 is penetrated by the transfer needle tip 57. Fluid is transferred from the fluid transfer device into the wide body receptacle 50. The wide body receptacle 50 is then removed from the shield 10.

Although the invention is described in terms of transferring fluid to a receptacle from a fluid collection device, persons skilled in the art should appreciate that fluid can be transferred to a receptacle using the method and apparatus of the present disclosure from any number of fluid container or transfer apparatus having a needle or cannula such as, for example, a transfer apparatus connected to a transfusion tube.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A transfer needle safety apparatus comprising:
    a shield having a wide diameter proximal end side-wall defining a cavity and a rim defining a substantially full diameter proximal opening, said shield having a narrower diameter distal end wall with an open tubular extension extending distally therefrom, said shield having an inner contour adapted to receive a wide body collection vessel; and
    a removable sleeve configured and dimensioned to be releasably retained within said cavity and self align coaxially therewith, said removable sleeve comprising an inner cylinder defining an open proximal end and an open distal end and having an inside diameter adapted for receiving a narrow body collection vessel;
    wherein the removable sleeve is configured and dimensioned to be positionable within the cavity of the shield such that a narrow body collection vessel can be received in the inner cylinder and the removable sleeve is configured and dimensioned to be removable from the cavity of the shield such that a wide body collection vessel having a width greater than the narrow body collection vessel can be received within the cavity of the shield.

2. A transfer needle safety apparatus according to claim 1 comprising a plurality of ribs extending radially from an outside surface of said inner cylinder to an inside diameter of said shield and cooperatively engaged therewith to provide coaxial alignment of said inner cylinder within said cavity of said shield.

3. A transfer needle safety apparatus according to claim 1 including a transfer needle non-removably installed with said shield, said transfer needle extending proximally into said cavity from said distal end wall, and distally into said tubular extension opening.

4. A transfer needle safety apparatus comprising:
    a shield having a wide diameter proximal end side-wall defining a cavity and a rim defining a substantially full diameter proximal opening, said shield having a narrower diameter distal end wall with an open tubular extension extending distally therefrom, said shield having an inner contour adapted to receive a wide body collection vessel, wherein said tubular extension is adapted to be mounted to a luer of a fluid transfer syringe; and
    a removable sleeve configured to be releasably retained within said cavity and self align coaxially therewith, said removable sleeve comprising an inner cylinder defining an open proximal end and an open distal end and having an inside diameter adapted for receiving a narrow body collection vessel;
    wherein the removable sleeve is configured and dimensioned to be positionable within the cavity of the shield such that a narrow body collection vessel can be received in the inner cylinder and the removable sleeve is configured and dimensioned to be removable from the cavity of the shield such that a wide body collection vessel having a width greater than the narrow body collection vessel can be received within the cavity of the shield.

5. A transfer needle safety apparatus according to claim 4 wherein said tubular extension includes mounting structure including threads adapted for attachment to a threaded luer of a fluid transfer syringe.

6. A transfer needle safety apparatus according to claim 4 wherein said tubular extension includes mounting structure in a distal end inside diameter of said tubular extension opening adapted for receiving a male luer of a fluid transfer syringe.

7. A transfer needle safety apparatus according to claim 4 wherein said tubular extension includes mounting structure including a luer lock fitting for removable attachment to a cooperating luer lock fitting of a fluid transfer syringe.

8. The transfer needle safety apparatus according to claim 1 wherein said open proximal end of said inner cylinder includes an annular flange extending to a diameter equal or greater than said proximal opening in said outer cylinder, and wherein said flange includes a rounded shoulder which blends into said open proximal end of said inner cylinder.

9. The transfer needle safety apparatus according to claim 1 wherein at least one slot is provided in said side-wall of said shield adjacent to said proximal opening to allow gripping and removal of said sleeve from said shield.

10. The transfer needle safety apparatus according to claim 1 wherein said removable sleeve includes a cylindrical proximal extension adjacent to said open proximal end to allow gripping and removal of said sleeve from said shield.

11. A transfer needle safety apparatus according to claim 1 wherein said shield proximal end side wall includes an internal undercut adjacent to said rim and wherein at least one of said ribs includes an inwardly formed step which engages said undercut when said sleeve is installed in said shield for removable retention of said sleeve in said cavity.

12. A transfer needle safety apparatus according to claim 1 comprising features incorporated with said sleeve and said shield to provide audible feedback indicating full insertion of said sleeve to said shield.

13. A transfer needle safety apparatus according to claim 2 wherein each of said ribs include an inclined distal end surface for aligning said sleeve with said shield when said inclined distal end surface engages said rim during installation of said sleeve to said shield.

14. A transfer needle safety apparatus comprising:
  a shield having a wide diameter proximal end side-wall defining a cavity and a rim defining a substantially full diameter proximal opening, said shield having a narrower diameter distal end wall with an open tubular extension extending distally therefrom, said shield having an inner contour adapted to receive a wide body collection vessel;
  a removable sleeve adapted to fit into said cavity and self align coaxially therewith, said removable sleeve comprising an inner cylinder defining an open proximal end and an open distal end and having an inside diameter adapted for receiving a narrow body collection vessel;
  a plurality of ribs extending radially from an outside surface of said inner cylinder to an inside diameter of said shield and cooperatively engaged therewith to provide coaxial alignment of said inner cylinder with said outside cylinder; and
  a transfer needle non-removably installed within said shield, said transfer needle extending proximally into said cavity from said distal end wall, and distally into said tubular extension opening;
  wherein each of said ribs extend far enough distally to engage said side-wall and ensure alignment of said sleeve within said shield before said distal end of said inner cylinder reaches said transfer needle tip during installation of said sleeve to said shield.

15. A transfer needle safety apparatus according to claim 14 wherein at least one of said ribs include a rib extension protruding distally therefrom and wherein said shield includes at least one clearance window configured to accept said rib extension.

16. A transfer needle safety apparatus comprising:
  a shield having a side-wall defining a cavity with a substantially full diameter proximal opening and having a narrower diameter distal end wall with an open tubular extension extending distally therefrom, said shield having an inside diameter adapted to receive a wide body collection vessel; and
  a removable sleeve adapted to fit into said cavity and self align coaxially therewith, said removable sleeve comprising an inner cylinder defining an open proximal end and an open distal end and having an inside diameter adapted for receiving a narrow body collection vessel; said open proximal end of said inside cylinder having a finger extending to a diameter equal or greater than said proximal opening in said shield.

17. A transfer needle safety apparatus according to claim 16 wherein said side-wall includes a slot disposed therein configured for receiving said finger of said removable sleeve.

18. A method of safety transferring body fluids to a vessel comprising:
  providing a shield having a side-wall defining a cavity with a rim defining a substantially full diameter proximal opening and having a narrower diameter distal end wall with an open tubular extension extending distally therefrom, said shield having an inside diameter adapted to receive a wide body collection vessel;
  providing a fluid transfer needle permanently installed within said shield and extending from the proximal end of said tubular extension into said cavity;
  providing a removable sleeve adapted to fit into said cavity and self align coaxially therewith, said removable sleeve comprising an inner cylinder defining an open proximal end and an open distal end and having an inside diameter adapted for receiving a narrow body collection vessel;
  securing a fluid transfer syringe to the distal end of said tubular extension;
  inserting the mouth of a narrow body fluid receptacle having a puncturable septum into said sleeve and puncturing said septum with said needle;
  transferring fluid from said syringe into said narrow body receptacle; and
  removing said narrow body receptacle from said sleeve.

19. The method according to claim 18 wherein said tubular extension includes mounting structure and wherein said luer is fitted to said tubular extension by cooperating structure disposed on said luer engaging said mounting structure.

20. The method according to claim 18 further comprising:
  removing said sleeve from said shield;
  inserting the mouth of a wide body fluid receptacle having a puncturable septum into said shield and puncturing said septum with said needle;
  transferring fluid from said syringe into said wide body receptacle; and
  removing said wide body receptacle from said shield.

* * * * *